United States Patent [19]

Schulz

[11] Patent Number: 4,908,202

[45] Date of Patent: Mar. 13, 1990

[54] USE OF 2-OXO-1-PYRROLIDINEACETAMIDE FOR THE DETERMINATION OF THE GLOMERULAR FILTRATION RATE IN HUMANS

[75] Inventor: Hans-Ulrich Schulz, Bad Schwartau, Fed. Rep. of Germany

[73] Assignee: Cassella Aktiengesellschaft, Frankfurt, Fed. Rep. of Germany

[21] Appl. No.: 299,793

[22] Filed: Jan. 23, 1989

[30] Foreign Application Priority Data

Feb. 2, 1988 [DE] Fed. Rep. of Germany ....... 3802996

[51] Int. Cl.$^4$ .................... A61K 49/00; A61K 31/40; G01N 31/00; G01N 33/48
[52] U.S. Cl. ........................................ 424/9; 514/424
[58] Field of Search ............................. 514/424; 424/9

Primary Examiner—Douglas W. Robinson
Assistant Examiner—Raymond J. Henley, III
Attorney, Agent, or Firm—Perman & Green

[57] ABSTRACT

The use of 2-oxo-1-pyrrolidineacetamide for the determination of the glomerular filtration rate in humans.

9 Claims, No Drawings

USE OF 2-OXO-1-PYRROLIDINEACETAMIDE FOR THE DETERMINATION OF THE GLOMERULAR FILTRATION RATE IN HUMANS

The present invention relates to the use of 2-oxo-1-pyrrolidineacetamide (piracetam) of the formula I

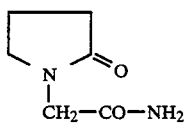

for the determination of the glomerular filtration rate in humans, and to a method for the determination of the glomerular filtration rate in humans.

The determination of the glomerular filtration rate is of great importance in connection with preclinical and clinical diagnostic and therapeutic measures, because it is generally possible with its aid to estimate the impairment of kidney function. The glomerular filtration rate (GFR) is defined as the amount of primary urine which is produced by all the glomeruli of both kidneys per unit time and which represents the ultrafiltrate of the blood. This glomerular filtration rate can, in principle, be determined with any substance which undergoes complete ultrafiltration, that is to say appears in the primary urine in the same concentration as in blood and, moreover, undergoes neither tubular secretion nor reabsorption from the primary urine.

In order to quantify the glomerular filtration rate the clearance of the particular test substance used is investigated, where, according to the van Slyke definition of the term, the clearance is defined as the apparent amount of plasma, in ml, from which a particular substance is removed in the kidneys in unit time (min).

In the past a very wide variety of clearance methods have been used and, of these, the endogenous creatinine clearance, the inulin clearance or the $^{51}$Cr-EDTA ($Na_2{}^{51}Cr$-ethylenediaminetetraacetate) clearance have achieved significance, for example, but they are also associated with a number of disadvantages (for example Henning, Klinische Laboratoriumsdiagnostik (Clinical Laboratory Diagnostic Methods) Urban & Schwarzenberg, Munich and Berlin 1960).

Thus, depending on the design of the particular clearance determination, there is a necessity for continuous infusion of the clearance substance and/or collection of urine which is associated with unpleasant catherization and/or multiple blood sampling. The use of radioactive test substances places an additional strain on the body.

It is to be regarded as a further disadvantage that many test substances are bound to endogenous protein, so that, when calculating the clearance, account has to be taken of a correction factor which is based on experience. This also applies, for example, to the method described in DE-A 3,224,041, which uses as test substancea corrinoid, in particular vitamin $B_{12}$.

2-Oxo-1-pyrrolidineacetamide (piracetam) is known and is commercially available as a nootropic drug.

It has now been found, surprisingly, that the use of 2-oxo-1-pyrrolidineacetamide for the determination of the glomerular filtration rate has considerable advantages over the state of the art.

The GFR can be measured simply by determinations of plasma levels, with the following method being used:

1. A test dose of 2-oxo-1-pyrrolidineacetamide is administered.
2. After a latency time of 2 hours, two blood samplings at different times are carried out.
3. The concentrations of 2-oxo-1-pyrrolidineacetamide in the resulting serum samples are measured, and a concentration/time plot on a semilogarithmic scale is constructed (blood level plot).
4. The clearance is calculated.

Both injection and oral administration of the test dose is possible. Amounts of 800 to 3,000 mg are normally given.

For the blood sampling, the second sampling normally takes place 2 to 3 hours after the first sampling. 1 to 2 ml of blood suffice for each. The concentration of the test substance is determined after extraction from the serum, advantageously by gas chromatography by a modification of the method of C. Hesse and M. Schulz (Chromatographia Vol. 12, No. 1 (1979) 12–16).

The clearance is advantageously calculated using the following formula:

$$Cl_{tot} = \frac{K_e \cdot V_d}{60} \text{ (ml/min)}$$

where
$Cl_{tot}$ = total body clearance
$K_e$ = elimination constant and
$V_d$ = volume of distribution (ml).

The elimination constant $K_e$ corresponds to the rate constant for the overall process of elimination from the bloodstream. It is obtained from the concentration/time plot on the semi-logarithmic scale using the following formula:

$$K_e = \frac{\ln c_1 - \ln c_2}{t_2 - t_1} \text{ (1/time)}$$

The $K_e$ measured for 2-oxo-1-pyrrolidineacetamide in a systematic investigation is 0.1398 1/h in healthy male subjects.

The volume of distribution $V_d$ of the substance in the human body is measured using the following formula:

$$V_d = \frac{D}{C_o} \text{ (ml)}$$

in which
D = dose of test substance administered and
$C_o$ = blood level at time t=0.

The quantity of $C_o$ corresponds to the intercept of the downsloping blood level plot on the semilogarithmic scale with the y axis at time t=0.

The use of 2-oxo-1-pyrrolidineacetamide yields clearance values which corresponds to those measured with the creatinine or inulin clearance. At the same time, it offers considerable advantages over the methods hitherto known. Thus, the elaborate collection of urine, which is associated with uncertainties even under clinical conditions, is avoided. It is merely necessary to take two blood samples each of 1–2 ml. The test substance can also be administered orally.

A particular advantage is that no interaction occurs between the test substance and other substances such as, for example, pharmaceuticals in patients receiving drug treatment. This is a helpful property, and especially in the analytical determination.

Finally, there is also no exposure of the body to radioactivity.

Overall, the invention is distinguished by great practicability and it thus repesents an enrichment of renal diagnostic methods.

EXAMPLE

Each of ten juvenile male subjects in a group received an injection of 1,200 mg of 2-oxo-1-pyrrolidineacetamide. After 2 hours, a blood sample of about 2 ml was taken from each and, after a further 2.5 hours, another sample again of about 2 ml. The concentration of the test substance in the blood samples was determined as follows:

An internal standard of 2-pyrrolidonepropionamide and 1 ml of acetone were added to 100 μl of serum sample and mixed in a Rotamixer for 20 min. The mixture was then centrifuged for 2 min, and the supernatant was decanted off and evaporated under $N_2$ at 62° C. Then 100 μl of acetone were added and mixed in a Rotamixer for 30 sec. 1.5 μl of this sample were injected into the gas chromatograph.

The gas chromatograph used was a Sichromat 1 from Siemens AG, equipped with an on-column injector, an $N_2$-selective detector and a Siemens type BD 60 integrator. The column used was a glass column of I.D. 2 mm, O.D. 6 mm and length 340 mm, employing as stationary phase Gaschrom Q, 120–140 mesh, coated with 10% carbowax 20M from WGA Werner Günther Analysentechnik, Pfungstadt.

The following conditions were used:

| Temperatures: | Oven: | 220° C. |
|---|---|---|
| | Injector: | 230° C. |
| | Detector: | 300° C. |
| | Detector current: | 770 mA |
| Gases: | Helium: | 45 ml/min |
| | Hydrogen: | 12 ml/min |
| | Combustion air: | 100 ml/min |

The concentrations of test substance can be measured from the chromatograms obtained in this way, which are of high quality and show no interfering peaks. The relation between the peak areas for the test substance and the internal standard is linear over a wide concentration range. Blood level plots were prepared, and $C_o$ was determined therefrom.

Finally, the clearance was calculated using the formula stated above. Table 1 compares the results with the creatinine clearance determined at the same time.

| Subject | Creatinine clearance (ml/min) | 2-Oxo-1-pyrrolidine-acetamide clearance (ml/min) |
|---|---|---|
| 1 | 125.9 | 120.93 |
| 2 | 137.75 | 123.53 |
| 3 | 156.64 | 151.90 |
| 4 | 107.90 | 116.91 |
| 5 | 127.83 | 127.38 |
| 6 | 131.74 | 130.97 |
| 7 | 135.44 | 118.06 |
| 8 | 128.68 | 145.84 |
| 9 | 121.08 | 136.66 |
| 10 | 156.47 | 131.08 |
| Mean | 141.30 | 134.95 |
| Standard deviation | 23.94 | 15.17 |

The values for the glomerular filtration rate measured with the two methods do not differ within the range of experimental accuracy and they correspond to the means for healthy male subjects measured using the inulin clearance (Goldring, W., Chassis, H.: Hypertension and hypertensive disease. The Commonwealth Fund, New York, 1944).

What is claimed is:

1. A method for determining the glomerular filtration rate of a urine-producing subject which comprises administering a suitable known dose between about 800 and 300 mg. of piracetam to said subject, withdrawing blood samples from said subject at spaced time intervals after an initial latency time, and measuring the differences in the amounts of piracetam present in said blood samples over said time intervals and calculating the clearance.

2. The method according to claim 1 for determining the glomerular filtration rate of a urine-producing subject which comprises the steps of:
   (a) administering said suitable known dose of piracetam to said subject
   (b) withdrawing blood samples from said subject at spaced time intervals after an initial latency time;
   (c) measuring the concentration of piracetam in each of said blood samples;
   (d) producing a concentration/time plot on a semilogarithmic scale for each of said blood samples, and
   (e) calculating the clearance or elimination constant as a measurement of the amount of blood from which the piracetam has been removed in the kidneys in unit time.

3. The method according to claim 1 in which said known dose of piracetam is about 1200 mg.

4. The method according to claim 1 in which said blood samples are between about 1 and 2 ml in volume.

5. The method according to claim 1 in which said initial latency time is about 2 hours or more.

6. The method according to claim 1 in which the time interval between said blood samples is about 2.5 hours or more.

7. The method according to claim 1 in which the concentration of piracetam in each of the blood samples is determined by gas chromatography after extraction from the blood serum.

8. The method according to claim 2 in which the elimination constant (Ke) equals:

$$\frac{\ln C_1 - \ln C_2}{t_2 - t_1}$$

wherein $\ln C_1$ and $\ln C_2$ are the semilogarithmic values of the concentrations of piracetam in the first and second blood samples, respectively, and $t_2 - t_1$ equals the time interval.

9. The method according to claim 8 in which total body clearance of the piracetam, in terms of ml/min equals $$\frac{KeVd}{60}$$

wherein Vd equals the volume of distribution of piracetam in milliliters.

* * * * *